United States Patent [19]

Francese et al.

[11] Patent Number: 4,803,298

[45] Date of Patent: Feb. 7, 1989

[54] PROCESS FOR THE PREPARATION OF PERFLUOROALKYL KETONES

[75] Inventors: Catherine Francese, L'Hay les Roses; Marc Tordeux, Sceaux; Claude Wakselman, Paris, all of France

[73] Assignee: Rhone-Poulenc Chimie, Courbevoie Cedex, France

[21] Appl. No.: 73,708

[22] Filed: Jul. 15, 1987

[30] Foreign Application Priority Data

Jul. 25, 1986 [FR] France ................................ 86 10988

[51] Int. Cl.$^4$ ............................................ C07C 51/373
[52] U.S. Cl. ...................................... 860/174; 560/51; 568/319; 568/397
[58] Field of Search ................ 568/397, 319; 560/174, 560/51

[56] References Cited

U.S. PATENT DOCUMENTS

| | | | |
|---|---|---|---|
| 3,449,371 | 7/1969 | Throckmorton | 560/174 |
| 3,481,986 | 12/1969 | Hall et al. | 560/174 |
| 4,136,121 | 1/1979 | Martini et al. | 568/397 |
| 4,484,993 | 11/1984 | Ishikawa et al. | 204/158 |

FOREIGN PATENT DOCUMENTS

| | | | |
|---|---|---|---|
| 0028778 | 5/1981 | European Pat. Off. | 545/40 |
| 615061 | 7/1978 | U.S.S.R. | 560/174 |

OTHER PUBLICATIONS

Reaction of Heptafluoro-1-Methylethylzinc Iodide w/Halides and Anhydrides of Carboxylic Acids; Sekiya et al., Chemical Abstracts, vol. 86, No. 19, May 9, 1977.
Reaction of Heptafluoro-1-Methylethylzinc Iodide w/Halides and Anhydrides of Carboxylic Acids; Sekiya et al., Chemistry Letters, pp. 81–84, 1977 (Published by the Chemical Society of Japan.
Synthesis of Ethyl 4-haloacetoacetates; Res. Discl. No. 116, Dec. 1977, No. 11662.,
Hexafluoroacetone; C. G. Krespan and W. J. Middleton; Fluorine Chemistry Reviews 1(1) pp. 145–196, (1967).

*Primary Examiner*—James H. Reamer
*Attorney, Agent, or Firm*—Finnegan, Henderson, Farabow, Garrett, & Dunner

[57] ABSTRACT

A process for the preparation of a perfluoroalkyl ketone. A perfluoroalkyl halide, zinc and an ester are brought into contact with one another. Preferably a polar aprotic solvent and/or a pyridine is also present.

12 Claims, No Drawings

PROCESS FOR THE PREPARATION OF PERFLUOROALKYL KETONES

The present invention relates to a process for the preparation of perfluoroalkyl ketones and, more particularly, to a process for the preparation of alkyl trifluoropyruvate, a perfluoroalkyl ketone. As is well-understood, a perfluoroalkyl ketone is a compound containing a —C(O)— group. At least one of the valences of the —C(O)— group is substituted by a perfluoroalkyl group. If only one valence of the —C(O)— group is substituted by a perfluoroalkyl group, the other valence is substituted by a group containing a carbon atom that is directly bonded to the —C(O)— group.

Krespan and Middleton, "Fluorine Chemistry Reviews 1, 145–196 (1967)" describe known methods for preparing perfluoroalkyl ketones, such as hexafluoroacetone. For example, in a first stage of the reaction, acetone reacts with chlorine and then, in a second stage, the hexachloroacetone obtained in the first stage reacts with hydrofluoric acid at 300° C. to effect chlorine-fluorine exchange.

The present invention differs from the prior art by reacting, in the presence of zinc, (1) a perfluoroalkyl halide of the formula (I)

$$Rf\ X \quad (I)$$

wherein X represents Br or I and Rf represents a perfluoroalkyl radical containing 1 to 12 carbon atoms in its chain; with (2) an ester of the formula (II)

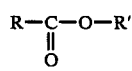

wherein R represents a cyano, perfluoroalkyl or alkoxycarbonyl group and R' represents an alkyl, aryl, alkylaryl or arylalkyl group.

Advantageously, at least one solvent selected from the group consisting of a polar aprotic solvent, preferably a dipolar aprotic solvent, and a pyridine is employed.

The invention is not limited to the above-mentioned illustrative groups defining R, but also includes all electron-attracting groups which have the same functions in the reaction as the perfluoroalkyl, alkoxycarbonyl or cyano groups.

The perfluoroalkyl iodides and bromides are preferably selected from the group consisting of trifluoromethyl bromide and perfluoroalkyl iodides, wherein the perfluorinated alkyl chain contains from 2 to 12 carbon atoms. This preference results from a difference in cost and not from a difference in reactivity of the compounds. Specifically, bromotrifluoromethane is much less expensive than iodotrifluoromethane and, conversely, perfluoroethyl and perfluorobutyl iodides are much less expensive than their brominated analogs. The use of trifluoromethyl bromide is most preferred.

Preferred esters of the formula (II) include those wherein R represents a perfluoroalkyl or alkoxycarbonyl group, such as trifluoroacetic acid and oxalic acid esters. The radical R' preferably represents a straight-chain or branched alkyl group containing 1 to 6 carbon atoms, or a phenyl group.

Representative compounds of the formula (II) include ethyl trifluoroacetate and ethyl oxalate.

Zinc is advantageously employed in a dispersed form to ensure the best contact with the gases or the liquids employed in the process of the invention. The particular shape and size of the zinc metal can be readily selected, without engaging in undue experimentation, by a worker of ordinary skill in the art according to the reactivity of the starting materials employed.

Representative polar aprotic solvents include dimethylformamide, dimethylsulfoxide, dimethylacetamide, N-methylpyrrolidone and hexamethylphosphoramide.

The use of at least one of dimethylformamide and a pyridine is preferred.

Representative pyridines include unsubstituted pyridine or a pyridine substituted with one or more alkyl groups, such as methyl- or dimethylpyridine. The use of unsubstituted pyridine is preferred.

The pyridine can enable the induction time of the reaction to be reduced significantly.

Preferably, a zinc: ester molar ratio greater than or equal to 1:1 and less than 2:1 and a perfluoroalkyl iodide or bromide: ester molar ratio greater than or equal to 1:1 are employed. If excess trifluoromethyl bromide is used, the bromide, being in gaseous form, can easily be recycled. The reaction temperature preferably ranges from $-20°$ C. to $100°$ C.

The reaction is preferably carried out in the absence of oxygen.

The pressure is preferably greater than or equal to atmospheric pressure and more preferably ranges from 1 to less than 10 bars.

Ethyl trifluoropyruvate and hexafluoroacetone are representative products obtained according to the process of the invention.

The reaction is carried out for a time sufficient to obtain the desired perfluoroalkyl ketone. Representative times range from 1 to 5 hours.

The products resulting from the present invention are useful in the synthesis of modified copolymers ("Fluorine Chemistry Reviews 1, 145–196, (1967)") or as synthesis intermediates in the manufacture of heterocyclic compounds (Journal of Fluorine Chemistry, 30 (1986) 463–468).

The invention will be described more completely using the examples below which should not be regarded as limiting the scope of the invention.

EXAMPLES

EXAMPLE 1

Ethyl Trifluoroacetate —CF$_3$Br 15 ml of pyridine, 5 g of ethyl trifluoroacetate (0.0352 mole) and 2.5 g of zinc powder (0.0385 mole) were placed in a thick glass flask.

The flask was placed in a Parr bomb. A vacuum was created therein and bromotrifluoromethane was introduced until a pressure of 3 bars was obtained. The pressure was maintained at between 4 and 2.6 bars during the reaction. The contents were stirred throughout the reaction period, which lasted 1.3 hours.

The contents were filtered and hydrolysis was then carried out using 50 ml of 10% hydrochloric acid while stirring for 30 minutes.

After extracting with ether, washing with water, drying over magnesium sulfate and evaporating off the solvent, the hexafluoroacetone was distilled in the hydrate form. b.p.=34°-36° C./20 mm Hg. 3.5 g (54%) were obtained.

(b.p. lit.=55°-56° C./80 mm Hg).

$^{19}F$ NMR spectrum (CFCl$_3$ ext.); −83.3 ppm (s, CF$_3$).

EXAMPLE 2:

Ethyl Oxalate —CF$_3$Br 50 ml of pyridine, 20 ml of ethyl oxalate (0.147 mole) and 10 g of zinc powder (0.154 mole) were placed in a thick glass flask.

The flask was placed in a Parr bomb. A vacuum was created therein and bromotrifluoromethane was introduced until a pressure of 3.6 bars was obtained; the contents were stirred throughout the reaction period, which lasted 1.5 hours, and the pressure was maintained at between 4 and 2.6 bars.

The contents were filtered and hydrolysis was then carried out using 50 ml of ice-cold 10% hydrochloric acid while stirring for 30 minutes.

After extracting with ether, washing with water, drying over magnesium sulfate and evaporating off the solvent, ethyl trifluoropyruvate was obtained in the hydrate form.

Dehydration was then carried out with concentrated sulfuric acid at ambient temperature to yield 9.5 g of ethyl trifluoropyruvate (38%), trapped under vacuum at −78° C. (B.p. lit.=89° C.).

$^{19}F$ NMR spectrum (CF Cl$_3$ ext.)=−75.7 ppm (s, CF$_3$).

$^1H$ NMR (TMS int.)=4.5 ppm (1, CH$_2$); 1.4 ppm (t, CH$_3$).

EXAMPLE 3

Ethyl Oxalate - C$_6$F$_{13}$I 10 ml of pyridine, 3 ml of ethyl oxalate (0.0221 mole) and 1.5 g of zinc powder (0.023 mole) were placed in a round-bottomed flask.

The flask was purged with argon and 10 g of 1-iodoperfluoro-n-hexane (0.022 mole) were then added, with stirring. The reaction was exothermic and lasted 2 hours.

The contents were filtered and hydrolysis was then carried out using 20 ml of ice-cold 10% hydrochloric acid while stirring for 30 minutes.

After extracting with ether, washing with water, drying over magnesium sulfate and evaporating off the solvent, ethyl 2-oxotridecafluorooctanoate was distilled. (B.p.=52°-58° C. (20 mm Hg)).

1.8 g (20%) were obtained.

$^{19}F$ NMR spectrum (CFCl$_3$ ext.): −80.7 ppm (t.t., CF$_3$);

−117 to −123 ppm (m, 8F);

−125 to −127 ppm (m, 2F).

We claim:

1. A process for the preparation of a perfluoroalkyl ketone of the formula $$R-\underset{\underset{O}{\|}}{C}-Rf,$$

wherein R and Rf are as defined below, comprising the step of bringing into contact with one another, in the presence of at least one solvent, for a time sufficient to form said perfluoroalkyl ketone:

(1) a perfluoroalkyl halide of the formula (I)

$$Rf\ X \quad (I)$$

wherein X represents Br or I and Rf represents a perfluoroalkyl radical containing 1 to 12 carbon atoms in its chain;

(2) zinc and (3) an ester of the formula (II)

$$R-\underset{\underset{O}{\|}}{C}-O-R' \quad (II)$$

wherein R represents a cyano, perfluoroalkyl or alkoxycarbonyl group and R' represents an alkyl, aryl, alkylaryl or arylalkyl group.

2. The process of claim 1 wherein said halide of formula (I), zinc, and said ester of formula (II) are brought into contact in at least one solvent selected from the group consisting of a polar aprotic solvent and a pyridine.

3. The process of claim 2, wherein said polar aprotic solvent is a dipolar aprotic solvent.

4. The process of claim 1, wherein the compound of formula (I) is trifluoromethyl bromide.

5. The process of claim 1, wherein the ester of formula (II) is a perfluoroalkylated acid ester.

6. The process of claim 1, wherein the ester of formula (II) is a trifluoroacetic acid ester or an oxalic acid ester.

7. The process of claim 3, wherein the dipolar aprotic solvent is dimethylformamide.

8. The process of claim 2, wherein the solvent is pyridine.

9. The process of claim 1, wherein the reaction temperature ranges from −20° C. to 100° C.

10. The process of claim 1, wherein the reaction pressure is greater than or equal to atmospheric pressure.

11. The process of claim 10 wherein the reaction pressure ranges from 1 to less than 10 bars.

12. The process of claim 1, wherein the zinc:ester molar ratio ranges from 1:1 to less than 2:1 and the perfluoroalkyl halide:ester molar ratio is at least 1:1.

* * * * *